United States Patent
Garigapati (10) Patent No.: US 10,124,063 B2
(45) Date of Patent: *Nov. 13, 2018

(54) STABLE COMPOSITIONS CONTAINING THROMBIN AND METHODS FOR PREPARATION AND USE THEREOF

(71) Applicant: Orthovita, Inc., Malvern, PA (US)

(72) Inventor: Venkat R. Garigapati, Southborough, MA (US)

(73) Assignee: Orthovita, Inc., Malvern, PA (US)

( * ) Notice: Subject to any disclaimer, the term of this patent is extended or adjusted under 35 U.S.C. 154(b) by 116 days.

This patent is subject to a terminal disclaimer.

(21) Appl. No.: 14/833,597

(22) Filed: Aug. 24, 2015

(65) Prior Publication Data

US 2015/0359892 A1    Dec. 17, 2015

Related U.S. Application Data (63) Continuation of application No. 13/794,421, filed on Mar. 11, 2013, now Pat. No. 9,149,529.

(60) Provisional application No. 61/717,906, filed on Oct. 24, 2012.

(51) Int. Cl.
| | |
|---|---|
| *A61K 38/48* | (2006.01) |
| *A61K 38/39* | (2006.01) |
| *A61K 47/12* | (2006.01) |
| *A61K 9/00* | (2006.01) |
| *A61K 9/08* | (2006.01) |
| *A61K 47/42* | (2017.01) |

(52) U.S. Cl.
CPC ............ *A61K 47/12* (2013.01); *A61K 9/0019* (2013.01); *A61K 9/08* (2013.01); *A61K 38/39* (2013.01); *A61K 38/4833* (2013.01); *A61K 47/42* (2013.01)

(58) Field of Classification Search
CPC ........ A61K 47/12; A61K 9/08; A61K 9/0019; A61K 38/4833; A61K 47/42; A61K 38/39; A61K 2300/00
See application file for complete search history.

(56) References Cited

U.S. PATENT DOCUMENTS

| | | |
|---|---|---|
| 4,515,637 A | 5/1985 | Cioca |
| 4,696,812 A | 9/1987 | Silbering et al. |
| 4,965,203 A | 10/1990 | Silbering et al. |
| 5,130,244 A | 7/1992 | Nishimaki et al. |
| 5,290,552 A | 3/1994 | Sierra et al. |
| 5,997,811 A | 12/1999 | Esposito |
| 6,096,309 A | 8/2000 | Prior et al. |
| 6,280,727 B1 | 8/2001 | Prior et al. |
| 7,351,561 B2 | 4/2008 | Metzner et al. |
| 7,473,543 B2 | 1/2009 | Jiang et al. |
| 8,071,090 B2 | 12/2011 | Senderoff et al. |
| 2003/0215455 A1* | 11/2003 | Reynolds ............... A61K 31/70 424/184.1 |
| 2006/0088518 A1 | 4/2006 | Jorquera Nieto et al. |
| 2006/0246052 A1 | 11/2006 | Okuda et al. |
| 2008/0003220 A1* | 1/2008 | Gokarn ................ A61K 9/0019 424/135.1 |
| 2008/0021104 A1* | 1/2008 | Tarallo ................. A61K 9/0095 514/557 |
| 2011/0045034 A1 | 2/2011 | Nur et al. |
| 2012/0164224 A1 | 6/2012 | Wang et al. |

FOREIGN PATENT DOCUMENTS

| | | |
|---|---|---|
| EP | 0277096 B1 | 7/1992 |
| EP | 0505604 B1 | 9/1996 |
| EP | 1221479 B1 | 11/2006 |
| EP | 1927658 B1 | 10/2012 |
| WO | 2004058943 A2 | 7/2004 |

OTHER PUBLICATIONS

Janjua H.S. et al. "Continuous infusion of a standard combination solution in the management of hyperkalemia", Nephrol. Dial. Transplant, Jan. 10, 2011, vol. 26, pp. 2503-2508.*
Walford S.N., "Composition of Cane Juice", Proc. S. Afr. Surg. Technol. Ass., 1996, vol. 70, pp. 265-266.*
Stromberg A. et al., "Manipulating the genetic identity and biochemical surface properties of individual cells with electric-field-induced fusion", PNAS, Jan. 4, 2000, vol. 97, No. 1, pp. 7-11.*
Hogberg C. et al., Succinate independently stimulates full platelet activation via cAMP and phosphoinositide 3-kinase-b signaling, Journal of Thrombosis and Haemostasis, 2011, vol. 9, pp. 361-372.

* cited by examiner

*Primary Examiner* — Satyendra K Singh
(74) *Attorney, Agent, or Firm* — Lerner, David, Littenberg, Krumholz & Mentlik, LLP

(57) ABSTRACT

Compositions comprising thrombin and collagen and methods of preparation thereof are disclosed herein. In one embodiment, a composition comprises thrombin and collagen in an aqueous buffer solution, wherein the buffer solution includes at least one of a first compound represented by Formula I: $R_1-C(O)-O^-M^+$, wherein $R_1$ is $-CH_3$, $-CH_2CH_2C(O)OH$, or $-CH_2CH_2C(O)O^-M^+$, and wherein $M^+$ is a monovalent ion; or a second compound represented by Formula II: $R_2-C(O)-O^-M^{2+}-O-C(O)-R_2$, wherein $R_2$ is $-CH_3$ or $-CH_2CH_3$, and wherein $M^{2+}$ is a divalent ion. In one embodiment, the buffer solution includes sodium acetate, calcium propionate, and sorbitol.

18 Claims, 4 Drawing Sheets

FIGURE 1

STABLE COMPOSITIONS CONTAINING THROMBIN AND METHODS FOR PREPARATION AND USE THEREOF

CROSS-REFERENCE TO RELATED APPLICATIONS

The present application is a continuation of U.S. patent application Ser. No. 13/794,421, filed Mar. 11, 2013, which claims the benefit of the filing date of U.S. Provisional Patent Application No. 61/717,906 filed Oct. 24, 2012, the disclosures of which are incorporated herein by reference.

BACKGROUND OF THE INVENTION

The invention relates to thrombin-containing compositions and more broadly to the stability of such compositions. The thrombin-containing compositions can be used for hemostasis applications.

Thrombin can be used in hemostasis applications to catalyze coagulation-related reactions. For example, thrombin can be used to catalyze the formation of fibrin which can aide in clotting formation in wounds. Collagen-thrombin compositions or their use in hemostasis applications can be found, for example, in U.S. Pat. Nos. 4,515,637, 4,696,812, 4,965,203, 5,130,244, 5,290,552, 5,997,811, 6,096,309, 7,473,543, 8,071,090, United States Patent Application Publication No. 2006/0088518, and European Patent Nos. EP0277096A2, EP1221479B, EP1927658A1, and EP0505604A1.

One exemplary commercial product which utilizes such a composition is Vitagel®, which includes thrombin, microfibrillar collagen, sodium chloride (NaCl), PEG 1000 and calcium chloride ($CaCl_2$), and is being marketed for hemostasis applications. While the stability of VITAGEL® is established, typical formulations require the product to be manufactured with high initial thrombin activity levels (e.g., about 800 IU/ml) in order to maintain an effective thrombin activity level (e.g., at least 300 IU/ml) over the entire shelf-life of the product. The addition of excess thrombin contributes to high manufacturing costs.

There remains a need for improved stability in compositions containing thrombin and collagen and methods for making the same.

BRIEF SUMMARY OF THE INVENTION

The present invention is directed to compositions comprising thrombin and collagen in an aqueous buffer solution. In some embodiments, the buffer solution includes at least one of a first compound represented by the following Formula I:

Formula I (I)

wherein R1 is $-CH_3$, $-CH_2CH_2C(O)OH$, or $-CH_2CH_2C(O)O^-M^+$, and wherein $M^+$ is a monovalent ion; or a second compound represented by the following formula II:

Formula II (II)

wherein $R_2$ is $-CH_3$ or $-CH_2CH_3$, and wherein $M^{2+}$ a divalent ion.

In some embodiments, the thrombin is bovine thrombin.

In some embodiments, the thrombin is recombinant thrombin.

In some embodiments, the collagen is microfibrillar collagen.

In some embodiments, the microfibrillar collagen is pepsinized.

In some embodiments, the buffer solution includes at least one sugar.

In some embodiments, the at least one sugar is selected from the group consisting of mannitol, sorbitol, sucrose, raffinose, and trehalose.

In some embodiments, the amount of the first compound ranges from about 0.01 to about 10% weight or volume of the composition.

In some embodiments, the amount of the second compound ranges from about 0.01 to about 10% weight or volume of the composition.

In some embodiments, the amount of the at least one sugar ranges from about 0.01 to about 10% weight or volume of the composition.

In some embodiments, M+ is a sodium ion ($Na^+$).
In some embodiments, R1 is $-CH_3$.
In some embodiments, R1 is $-CH_2CH_2C(O)O^-M^+$.
In some embodiments, $M^{2+}$ is a calcium ion ($Ca^{2+}$).
In some embodiments, $R_2$ is $-CH_3$.
In some embodiments, $R_2$ is $-CH_2CH_3$.
In some embodiments, the pH of the composition ranges from about 5.0 to about 7.0.
In some embodiments, the pH of the composition ranges from about 5.5 to about 6.5.
In some embodiments, the pH of the composition ranges from about 5.6 to about 6.0.
In some embodiments, the buffer solution comprises a compound for adjusting the pH of the composition.
In some embodiments, the compound is selected from the group consisting of hydrochloric acid (HCl) and sodium hydroxide (NaOH).
In some embodiments, thrombin activity ranges from about 400 units to about 800 units of enzyme activity per milliliter of buffer solution.
In some embodiments, thrombin activity ranges from about 400 to about 500 units of enzyme activity per milliliter of buffer solution.
In some embodiments, $M^+$ is a sodium ion ($Na^+$), $R_1$ is $-CH_3$, $M^{2+}$ is a calcium ion ($Ca^{2+}$) and $R_2$ is $-CH_2CH_3$, and wherein the buffer solution further comprises sorbitol.
In some embodiments, the first compound is sodium acetate, the second compound is calcium propionate, and the buffer solution further comprises sorbitol.
In some embodiments, the buffer solution includes the second compound, and further comprises sorbitol.
In some embodiments, the buffer solution includes a first compound selected from the group consisting of sodium acetate and sodium succinate.

In some embodiments, the buffer solution includes a second compound selected from the group consisting of calcium propionate and calcium acetate.

In some embodiments, the buffer solution includes sodium acetate, calcium propionate, and sorbitol.

In some embodiments, the buffer solution includes sodium succinate, calcium propionate, and sorbitol.

In some embodiments, the sodium succinate is dibasic.

In some embodiments, the buffer solution include calcium acetate and sorbitol.

In some embodiments, the buffer solution includes calcium acetate and mannitol.

In some embodiments, the pH of the composition ranges from about 5.5 to about 6.5.

In some embodiments, wherein the pH of the composition ranges from about 5.6 to about 6.0.

Methods of making these compositions and methods of using these compositions in hemostasis applications are also part of the invention.

DETAILED DESCRIPTION

The present invention will be described in more detail below.

All percentages and ratios used herein are by weight of the total composition and all measurements made are at about room temperature and normal pressure unless otherwise designated. "Room temperature" as defined herein means a temperature ranging between about 22° C. and about 26° C. All temperatures are in degrees Celsius unless specified otherwise.

The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

As used herein, "consisting essentially of" means that the invention may include ingredients in addition to those recited in the claim, but only if the additional ingredients do not materially alter the basic and novel characteristics of the claimed invention. Preferably, such additional ingredients will not be present at all or only in trace amounts. However, it may be possible to include up to about 10% by weight of materials that could materially alter the basic and novel characteristics of the invention as long as the utility of the compounds (as opposed to the degree of utility) is maintained.

As used herein, "thrombin activity" is defined as International Unit of active thrombin per milliliter of buffer solution (IU/ml). Thrombin activates the fibrinogen to generate fibrin which polymerizes into fibers, e.g., a clot. The amount of the thrombin activity of the test sample is determined by measuring the time required to generate fibers on fibrometer and comparing it to a known standard. The procedures involves buffer preparation, fibrometer set up, coagulation control preparation, standard curve preparation, test sample preparation and measurement. One exemplary procedure for determining thrombin activity is described herein.

As used herein, "initial thrombin activity" is thrombin activity at manufacture of a composition of the present invention. The initial thrombin activity is representative of an initial amount of thrombin added to a composition of the present invention, where the initial amount of thrombin added is sufficient to maintain an effective thrombin activity of at least about 300 IU/ml over the shelf-life of a composition of the present invention. As used herein, "effective thrombin activity" is thrombin activity of at least about 300 IU/ml.

All ranges recited herein may include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

It should be further understood that a description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.3, 3, 4, 5, 5.7 and 6. This applies regardless of the breadth of the range.

Note that while the specification and claims may refer to a final product containing a certain reactant or a certain amount of, for example, a first compound represented by formula I such as sodium acetate, it may be difficult to tell from the product that any particular recitation is satisfied. Such a recitation may be satisfied, however, if the materials used prior to final production, for example, meet that recitation. Indeed, as to any property or characteristic of a final product which cannot be ascertained from the final product directly, it is sufficient if that property resides in the components recited just prior to production steps used to make the composition.

The term "storage stable" as used herein means that the composition maintains an effective thrombin activity over the shelf-life of the composition. The shelf-life of the composition may be up to about 8 years. In some embodiments, the shelf-life may range from about 3 to about 8 years when stored under refrigerated temperatures ranging from about 2° C. to about 8° C.

The effective thrombin activity and/or shelf-life of a composition may vary based on temperature conditions.

At room temperature and/or refrigerated temperature at the above-mentioned temperatures ranges, effective thrombin activity of a composition of the present invention, and having an initial thrombin activity ranging from about 300 IU/ml to about 800 IU/ml, may be maintained for at least about 2 years. In some embodiments, the effective thrombin activity may be maintain for a period ranging from about 2 to about 8 years. In further embodiments, the period may be at least about 5 years.

Thrombin

Thrombin used in accordance with the composition of the present invention can be selected from a group consisting of bovine thrombin or recombinant thrombin. Bovine thrombin and recombinant thrombin can be collected, synthesized, and/or purified by methods known in the art. Bovine thrombin may pose immunogenicity which can be minimized by substituting with human recombinant origin in hemostat formulations. Both bovine and recombinant thrombin are currently being marketed in the liquid or lyophilized form either stand alone or in combination with collagen/gelatin scaffolds or flowable collagen/fibrinogen for hemostasis applications.

The amount of thrombin in compositions of the prior art may vary from lot to lot based on variation in thrombin activity units in each lot of thrombin. Furthermore, excess thrombin can be required, for example, at least about 800 IU/ml, in order to maintain an effective thrombin activity over the shelf-life of the composition. One advantage of compositions of the present invention is that the amount of thrombin in a composition may be more standardized. Another advantage is the use of less initial thrombin used to form the composition due to improved stability of the composition over the shelf-life thus resulting in cost savings.

The initial amount of thrombin in a composition of the present invention may be measured in units of thrombin activity, i.e., IU/ml. The initial amount of thrombin, or said another way, the initial thrombin activity may range from about 50 IU/ml to about 1200 IU/ml of the composition. In some embodiments, the initial thrombin activity may range from about 100 IU/ml to about 800 IU/ml of the composition. In other embodiments, the initial thrombin activity may range from about 200 IU/ml to about 600 IU/ml of the composition. In yet another embodiment, the initial thrombin activity may range from about 400 IU/ml to about 500 IU/ml of the composition. In one embodiment, such as when calcium acetate is used as the second compound, the initial thrombin activity ranges from about 200 IU to about 600 IU. In a further embodiment, the initial thrombin activity may range from about 400 IU/ml to about 500 IU/ml of the composition. In another embodiment, such as when sodium acetate is used as the first compound and calcium propionate is used as the second compound, the amount of thrombin ranges from about 200 IU to about 600 IU. In a further embodiment, the initial thrombin activity may range from about 400 IU/ml to about 500 IU/ml of the composition.

Collagen

It should be understood that various types of collagen may be used in the present invention, including for example native collagen or native-type collagen, pepsinized microfibrillar collagen (i.e., soluble collagen having minimal cross-linking), alkaline-modified (limed) collagen, non-microfibrillar collagen, and other forms such as the types of collagen made by the processes disclosed in U.S. Pat. Nos. 6,096,309, and 6,280,727, both of which are incorporated by reference herein as if fully set forth herein.

In some embodiments, the collagen used in compositions of the present invention may have properties that make it suitable for injection in a subject. Such properties may include solubility, or other properties that allow for a composition including the collagen to be injectable. For example, compositions of the present invention can include microfibrillar collagen. In a further embodiment, the microfibrillar collagen may be pepsinized. In yet a further embodiment, the composition may not include non-microfibrillar collagen. In another embodiment, a composition that is homogeneous, and does not include any pockets of insoluble fibrils, can be used. Pockets of insoluble fibrils can form a heterogeneous solution, which can make the composition difficult to inject.

The amount of collagen in a composition of the present invention may ranges from about 5 mg/ml to about 50 mg/ml weight or volume of the composition, or from about 10 mg/ml % to about 40 mg/ml %, or from about 15 mg/ml % to about 30 mg/ml %. In some embodiments, such as when a mixture of non-microfibrillar and microfibrillar collagen is used, the amount of non-microfibrillar collagen ranges from about 5% to about 95% and the amount of microfibrillar collagen ranges from about 5% to about 95%. In one embodiment, such as when calcium acetate is used as the second compound, the amount of collagen ranges from about 10 mg/ml to about 30 mg/ml. In another embodiment, such as when sodium acetate is used as the first compound and calcium propionate is used as the second compound, the amount of collagen ranges from about 10 mg/ml to about 30 mg/ml.

Buffer Solution

A buffer solution used in accordance with the present invention includes one or more stabilizers in an aqueous medium. The one or more stabilizers are used to stabilize thrombin in a composition of the present invention, such that the composition is storage stable. The one or more stabilizers can include one or more of the first compound, the second compound, or one or more sugars as discussed below. The buffer solution can include a compound for adjusting the pH of the composition as discussed below. The buffer solution is capable of maintaining a storage stable composition over a broad pH range, from about 4.0 to about 7.0.

Stabilizer: First Compound

One stabilizer suitable for the composition of the present invention is a first compound represented by the following formula I:

Formula I $R_1$ is —$CH_3$, —$CH_2CH_2C(O)OH$, or —$CH_2CH_2C(O)O$-$M+$; $M^+$ is a monovalent atom, which can include any suitable monovalent atom found in the Periodic Table, such as in Group I or among the transition metals. In some embodiments, $M^+$ is sodium ion (Na+). Though having no desire to be bound by theory, the first compound may provide $M^+$ to stabilize thrombin in the composition. Further, the first compound may have buffer capacity to control pH of the composition. For example, when a strong acid is introduced into a composition, or otherwise H+ ions are introduced, $^-O$—$C(O)$—$R_1$ ions can form a stable compound with the H+ ions in solution, thus limiting their impact on pH. The first compound can be used alone or in combination with one or more additional stabilizers. Exem- plary first compounds include a sodium salt of a dicarboxylic acid, such as sodium succinate mono or di-basic, or sodium acetate.

The amount of the first compound ranges from about 0.01 to about 10% weight or volume of the composition. In one embodiment, the amount of the first compound ranges from about 0.1% to about 5%. In another embodiment, the amount of the first compound ranges from about 0.2% to about 2%. In one embodiment, such as when $R_1$ is —$CH_3$, the amount of the first compound ranges from about 1 mg/ml to about 50 mg/ml. In another embodiment, such as when R1 is other than —$CH_3$, the amount of the first compound ranges from about 1 mg/ml to about 50 mg/ml.

Stabilizer: Second Compound

One stabilizer suitable for the composition of the present invention is a second compound represented by the following formula II:

Formula II $R_2$ is —$CH_3$, —$CH_2CH_3$, or —$CH(CH_3)OH$; $M^{2+}$ is a divalent atom, which can include any suitable divalent atom found in the Periodic Table, such as in Group II or among the transition metals. In some embodiments, $M^{2+}$ calcium ion ($Ca^{2+}$). Though having no desire to be bound by theory, the second compound may provide $M^{2+}$ stabilize thrombin in the composition. Further, remaining ions of the second compound, i.e., $^-O$—$C(O)$—$R^2$, may bind to positively charged locations on thrombin to provide further stabilization. The second compound can be used alone or in combination with one or more additional stabilizers. Exemplary second compounds include a calcium salt of short chain fatty acid, such as calcium propionate, calcium acetate monohydrate, calcium lactate monohydrate, or the like.

The amount of the second compound ranges from about 0.01 to about 10% weight or volume of the composition. In one embodiment, the amount of the second compound ranges from about 0.1% to about 5%. In another embodiment, the amount of the second compound ranges from about 0.2% to about 2%. In one embodiment, such as when $R_2$ is —$CH_3$, the amount of the second compound ranges from about 1 mg/ml to about 50 mg/ml. In another embodiment, such as when $R_2$ is —$CH_2CH_3$, the amount of the second compound ranges from about 1 mg/ml to about 50 mg/ml.

Stabilizer: Sugar

One stabilizer suitable for the composition of the present invention is a sugar. The composition of the present invention can include at least one sugar. In some embodiments, the sugar can include one or more non-reducing saccharides. The sugar can be used to stabilize thrombin by establishing hydrogen bonding interactions with the thrombin protein structure. The hydrogen bonding interactions can preserve folding patterns of the thrombin protein structure in the composition. Exemplary sugars that can be used in the composition of the present invention include one or more sugars selected from the group consisting of mannitol, sorbitol, sucrose, raffinose, and trehalose.

The amount of sugar ranges from about 0.01 to about 10% weight or volume of the composition. In one embodiment, the amount of the sugar ranges from about 0.1% to about 5%. In another embodiment, the amount of the sugar ranges from about 0.2% to about 2%. In one embodiment, such as when the sugar is sorbitol, the amount of the sugar ranges from about 10 to 100 mg/ml. In a further embodiment, the amount of sorbitol ranges from about 25 to about 75 mg/ml. In another embodiment, such as when the sugar is mannitol, the amount of the sugar ranges from about 10 to about 100 mg/ml. In a further embodiment, the amount of mannitol ranges from about 25 to about 75 mg/ml.

Stabilizer: No Chlorine-Containing Salts

One stabilizer that may not suitable for a composition in accordance with the present invention is a chlorine-containing salt. Exemplary chlorine-containing salts can include sodium chloride (NaCl) and Calcium Chloride ($CaCl_2$). The inventors have discovered that chlorine-containing salts fail to provide sufficient stability to thrombin over the desired storage period. Specifically, chlorine-containing salts fail provide buffer capacity, as chlorine ions do not form a stable compound with $H^+$ ions in solution. Unlike NaCl, the first compounds of the present invention can provide $M^+$ ions to stabilize thrombin as well as $^-O$—$C(O)$—$R_1$ ions which have buffer capacity. Similarly, unlike $CaCl_2$, the second compounds of the present invention can provide $M^{2+}$ to stabilize thrombin instead of calcium chloride which has no buffer capacity. Any chlorine-containing salts that may exist in the compositions of the present invention are present in trace amounts that may not substantially contribute to stabilizing properties of the composition. Any trace amounts of a chlorine-containing salt that may exist in the compositions may result as reaction byproducts of components, such as stabilizers or other compounds, which were added to the composition.

Compound for Adjusting pH

One or more compounds for adjusting the pH of a composition in accordance with the present invention can be included. The one or more compounds can be utilized to raise or lower the pH of the composition. Exemplary compounds include hydrochloric acid (HCl) and sodium hydroxide (NaOH); however, other compounds are possible. The one or more compounds can be used to adjust the pH of the composition over a broad range. The pH of the composition can range from about 4.0 to about 7.0, or from about 5.0 to about 7.0, or from about 5.0 to about 6.0, or from about 5.5 to about 6.5, or from about 5.6 to about 6.0.

Some non-limiting, exemplary buffer solutions that may be utilized in the composition of the present invention may include sodium succinate, calcium propionate, and sorbitol; sodium succinate dibasic, calcium propionate, and sorbitol; or sodium acetate, calcium propionate, and sorbitol; or sodium acetate, calcium propionate, and mannitol; or calcium acetate and sorbitol; or calcium acetate and mannitol.

Methods for Preparation of a Composition

One exemplary method for preparation of an aqueous buffer solution includes preparation of an aqueous sugar solution by dissolving an amount of sugar in water. In some embodiments, the sugar solution may include about 2.5 to about 10% sugar by weight/volume. The water used to prepare the sugar solution may be water suitable for injection into the human body. At least one of the first or second compounds may then be dissolved into the sugar solution. For example, the first and/or second compounds can be added to the sugars solution in amount ranging from about 1 mg/ml to about 50 mg/ml of the sugar solution of each of the first and/or second compounds. A compound for adjusting the pH may then be added to the solution to formulate an aqueous buffer solution having the desired pH.

To form a composition, thrombin is added to the aqueous buffer solution. Thrombin may be dissolve in an amount, such that the initial thrombin activity ranges from about 100 IU/ml to about 1200 IU/ml of the buffer solution. In a further embodiment, the initial thrombin activity may range from about 200 IU/ml to about 600 IU/ml. In yet a further embodiment, the initial thrombin activity may range from about 400 IU/ml to about 500 IU/ml. Next, collagen is added to the buffer solution in an amount ranging from about 15 mg/ml to about 50 mg/ml of buffer solution. The buffer solution can be mixed and/or vortexed for several minutes to homogenize the composition. Optionally, a compound for adjusting the pH can be added to the composition to further adjust the pH to a desired level. The composition can be then be stored in a syringe (or any suitable storage device) and incubated at various temperatures to study stability and degradation as discussed below.

Measurement Methods

In one exemplary non-limiting embodiment, the stability of thrombin can be determined by a series of measurements after specific time intervals while the composition is stored at various temperatures. For example, the temperatures used may include about 37° C. and about 60° C. For example, a temperature of about 37° C. can be used to study the stability of a composition over a period of several months, whereas a temperature of about 60° C. can be used to study the degradation of the composition over a period of about one day or a few days.

The stability of thrombin can be determined by measuring clotting time for the composition. In one exemplary non-limiting embodiment, clotting time can be determined by first incubating a composition in an incubator at a desired temperature, i.e., about 37° C. if determining stability, or about 60° C. if determining degradation. The incubating composition may be disposed in a syringe. At specific time intervals, a portion of the composition is removed from the syringe for analysis. Prior to removal, the composition is mixed thoroughly, for example, by opening the syringe cap and connecting to another empty syringe with a connector and flushing the composition back and forth for several times prior to take a known amount of composition for analysis. The known amount is diluted with the corresponding buffer solution and mixed thoroughly. A portion of the known amount is transferred to a container, such as a cuvette containing a magnetic element, such as a magnetic spherical ball, and further diluted with the corresponding buffer solution. The container was placed an instrument which rotates the magnetic element in container while the container is maintained at the desired temperature. Initially, the magnetic element can rotate freely because the solution is typically thin. Plasma protein solution is added to the container. Thrombin from the composition reacts with plasma protein and collagen from the composition to form fibrin like material thus it prevents bleeding. For example, fibrin gel can be formed. The magnetic element cannot rotate freely, if at all, in a fibrin gel. The time need to form the gel is recorded as the clotting time. For example, a shorter clotting time indicates the thrombin is more active. If the composition is stable throughout the storage, all time points of analysis show consistent clotting time. If the composition is not stable, a longer clotting time is symptomatic of loss in thrombin activity and ultimately the composition can fail to form a gel.

Thrombin activity can be determined by comparing the clot time to a relationship generated from a known standard stock solution having a specific thrombin activity. For example, the standard stock solution can be diluted to generate a series of diluted stock solutions having known thrombin activity based on the standard stock solution. The series of diluted stock solutions can be measured in the same manner as discussed above to determine the clot time of each diluted stock solution. A graph of clot time versus thrombin activity can be generated from the clot time measurements of each diluted stock solution. A relationship between clot time and thrombin activity can be determined from the graph, such as by fitting the data or any suitable known method. The relationship can then be used to determine thrombin activity from clot times in experimental samples.

Examples of compositions of the present invention, methods of making and measurements of the same are shown below.

Examples 1-3

Preparation of a Buffer Solution

Sugar 10% solution: 10 g of sugar was weighed and carefully transferred into a 100 ml of volumetric flask to which about 70 ml Water for Injection (WFI) was added while slightly swirling the flask until the sugar completely dissolved. Finally more WFI was added to the mark of 100 ml. About 20 mg to about 1000 mg of the first compound and about 20 mg to about 1000 mg of the second compound were dissolved in 20 ml of 10% sugar solution. Using about 0.01N HCl solution and/or 0.01 NaOH solution, the pH of the buffer solution was adjusted ranging from about 5.0 to about 8.5.

Composition Preparation:

About 2000 IU of lyophilized bovine thrombin was dissolved in about 2 ml of the buffer solution. About 2 g of collagen was added and mixed for about 2-3 minutes to yield a homogenous solution of about 4 ml. The solution had an initial thrombin activity of about 500 IU/ml. The composition was transferred into a syringe, labeled and closed with a cap.

Clot Time Measurement:

Syringes containing the composition were kept in an incubator at 37° C. At specific time intervals, the contents of the syringe were mixed thoroughly prior to the sampling for analysis by connecting to another empty syringe and flushing the material back and forth for about 3 times prior to take a known amount of composition for analysis.

The know amount of composition was weighed and diluted with the buffer solution up to about 8 times the weight of the know amount and mixed thoroughly for about a minute. About 10 µL of diluted solution was transferred to a cuvette containing a magnetic spherical ball, which was further diluted with about 90 µL of the buffer solution. The cuvette was placed on Diagnostica Stago Start Hemostasis Analyzer, manufactured by Stago, at 37° C. At this time, the magnetic spherical ball rotates freely as the solution is very thin. The clot time was measured by adding about 100 µL of plasma protein solution to the sample cuvette. Thrombin reacts with plasma protein and collagen to form fibrin like material thus it prevents bleeding. The spherical ball couldn't rotate in the magnetic field and the time needed to form a gel like material was automatically recorded by the instrument as the clot time.

Thrombin activity can be determined from the clot time measurements using a relationship between clot time and thrombin activity as discussed above.

The buffer solution of Example 1 was prepared using about 4 g of sorbitol, about 164 mg of sodium succinate dibasic, about 236 mg of calcium propionate in about 20 ml of water, and having a pH of about 5.9.

The buffer solution of Example 2 was prepared using about 4 g of sorbitol, about 164 mg of sodium acetate, about 236 mg of calcium propionate in about 20 ml of water, and having a pH of about 5.78.

The buffer solution of Example 3 was prepared using about 4 g of mannitol, about 164 mg of sodium acetate, about 236 mg of calcium propionate in about 20 ml of water and having a pH of about 5.78.

Clotting times for Examples 1-3 are shown below in Table 1.

Comparative Examples 1-2

Comparative examples 1-2 include stabilizing components that can be found a buffer solution used for VITAGEL®.
Preparation of a Buffer Solution:

A buffer solution having about 1 mg/ml to about 10 mg/ml of PEG1K (polyethylene glycol, 1000 repeat units), about 1 mg/ml to about 20 mg/ml of the NaCl and about 1 mg/ml to about 20 mg/ml of the $CaCl_2$ was prepared. Using about 0.01N HCl solution, the pH of the buffer solution was adjusted ranging from about 5 to about 6.

The composition preparation and the clotting time measurements of Comparative Examples 1-2 are the same as those described above for Examples 1-3.

The buffer solution of Comparative Example 1 was prepared using about 40 mg of PEG1K, about 176 mg of NaCl, about 116 mg of $CaCl_2$ in about 20 ml of water, and having a pH of about 5.7.

The buffer solution of Comparative Example 2 was prepared using about 40 mg of PEG1K, about 176 mg of NaCl, about 116 mg of $CaCl_2$ in about 20 ml of water, and having a pH of about 5.9.

TABLE 1

Stability at 37° C.

| | | Day | | | | | |
|---|---|---|---|---|---|---|---|
| | pH | 1 | 9 | 22 | 35 | 57 | 71 | 90 |
| | | Clotting time (sec) | | | | | |
| Example 1 | 5.9 | 36.3 | 39.2 | 31 | 45.4 | 38 | 41.5 | 41 |
| Example 2 | 5.78 | 29 | 28.4 | 28 | 30 | 24 | 28.1 | 27.5 |
| Example 3 | 5.78 | 28.5 | 28.8 | 19.5 | 28.2 | 27 | 33.1 | 29.8 |
| Comparative Example 1 | 5.7 | 10.9 | 23 | 23 | 100 | 100 | 100 | 100 |
| Comparative Example 2 | 5.9 | 9.9 | 60 | 100 | 100 | 100 | 100 | 100 |

| | Day | | | |
|---|---|---|---|---|
| | 111 | 132 | 154 | 177 |
| | Clotting time (sec) | | | |
| Example 1 | 49.7 | 59.8 | 100 | 100 |
| Example 2 | 34.7 | 44 | 55.9 | 78.4 |
| Example 3 | 40 | 47.8 | 62.8 | 100 |
| Comparative Example 1 | 100 | 100 | 100 | 100 |
| Comparative Example 2 | 100 | 100 | 100 | 100 |

Figure 1:
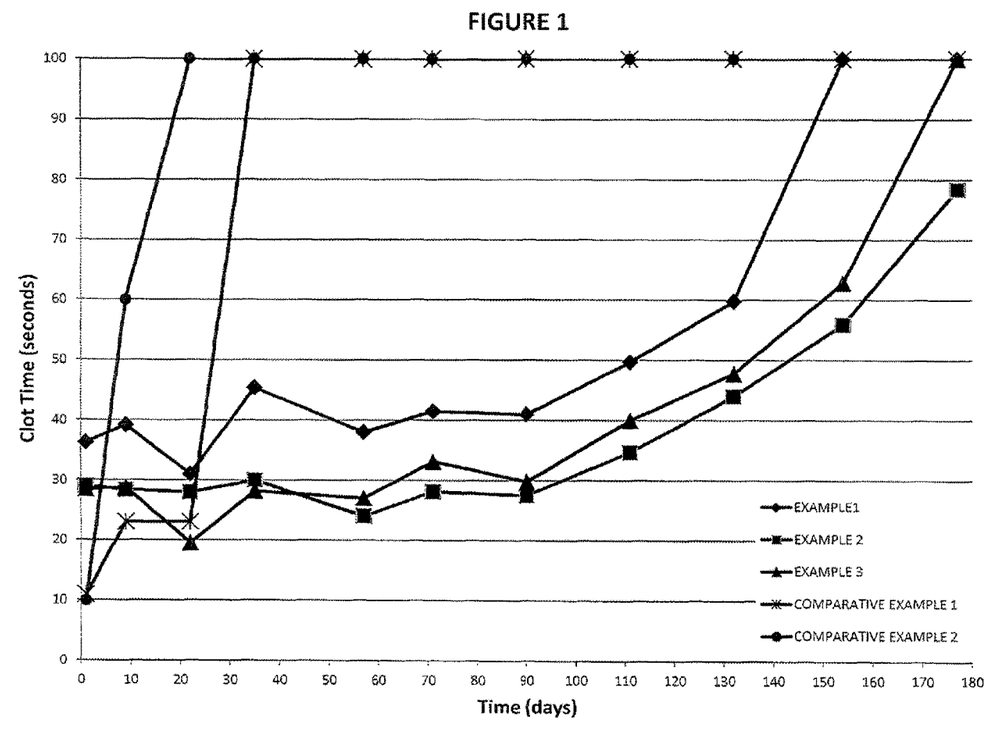
FIG. 1 depicts stability behavior at accelerated temperature in accordance with some embodiments of the present invention.

The data in Table 1 is represented in graphical form in FIG. 1. As shown in FIG. 1, Examples 1-3 exhibit a clotting time below about 50 seconds for at least about 90 days. Example 1 exhibited a clotting time of about 60 seconds after 154 days. In contrast, Comparative Examples 1 and 2, which include stabilizing components present in a buffer solution used for VITAGEL®, did not exhibit clot times below 40 seconds after less than 35 days.

The data in Table 1 indicates that compositions of Examples 1, 2 and 3 were more stable than those of Comparative Examples 1 and 2. In some embodiments, compositions, such as in Example 2 containing sodium acetate, calcium propionate, and sorbitol may be more stable than compositions, such as in Example 1, which contains sodium succinate dibasic, calcium propionate and sorbitol. In a further embodiment, compositions, such as in Example 2, may also be more stable than compositions, such as in Example 3, which contains sodium acetate, calcium propionate, and mannitol. Comparative Examples 1 and 2 were also pH sensitive as shown by the data in Table 1 and in FIG. 1. Comparative example 1 at pH 5.7 can be more stable than Comparative Example 2 at pH 5.9. Examples 1-3 did not exhibit much sensitivity to change in pH.

Current invention demonstrates that Thrombin is more stable in sorbitol buffer containing sodium acetate and calcium propionate than any other buffer and it is far superior to vitagel product.

Examples 4-5

Prepared and measured as discussed above for corresponding Examples 2-3, except at pH of 5.8 and incubation and measurement temperature of about 60° C.

Examples 6-7

Prepared and measured as discussed above for corresponding Examples 2-3, except at pH of 6.5 and incubation and measurement temperature of about 60° C.

Comparative Examples 3-4

Prepared and measured as discussed above for corresponding Comparative Examples 1-2, except at pH of 5.83 and 6.4, respectively, and incubation and measurement temperature of about 60° C.

TABLE 2

Stability at 60° C.

| | | Time (hours) | | | | | | |
|---|---|---|---|---|---|---|---|---|
| | pH | 0 | 0.5 | 1 | 2 | 4 | 8 | 18 |
| | | Clotting time (sec) | | | | | | |
| Example 4 | 5.8 | 13.6 | 14.9 | 16.2 | 23.6 | 41.9 | 100 | 100 |
| Example 5 | 5.8 | 13.6 | 17.6 | 17.7 | 23.2 | 100 | 100 | 100 |
| Example 6 | 6.5 | 13.8 | 15.1 | 15.4 | 29.7 | 100 | 100 | 100 |
| Example 7 | 6.5 | 13.6 | 15.5 | 16 | 73.7 | 100 | 100 | 100 |
| Comparative Example 3 | 5.83 | 12.6 | 10.8 | 15.8 | 100 | 100 | 100 | 100 |
| Comparative Example 4 | 6.4 | 43.3 | 44.5 | 50.7 | 100 | 100 | 100 | 100 |

Figure 2:
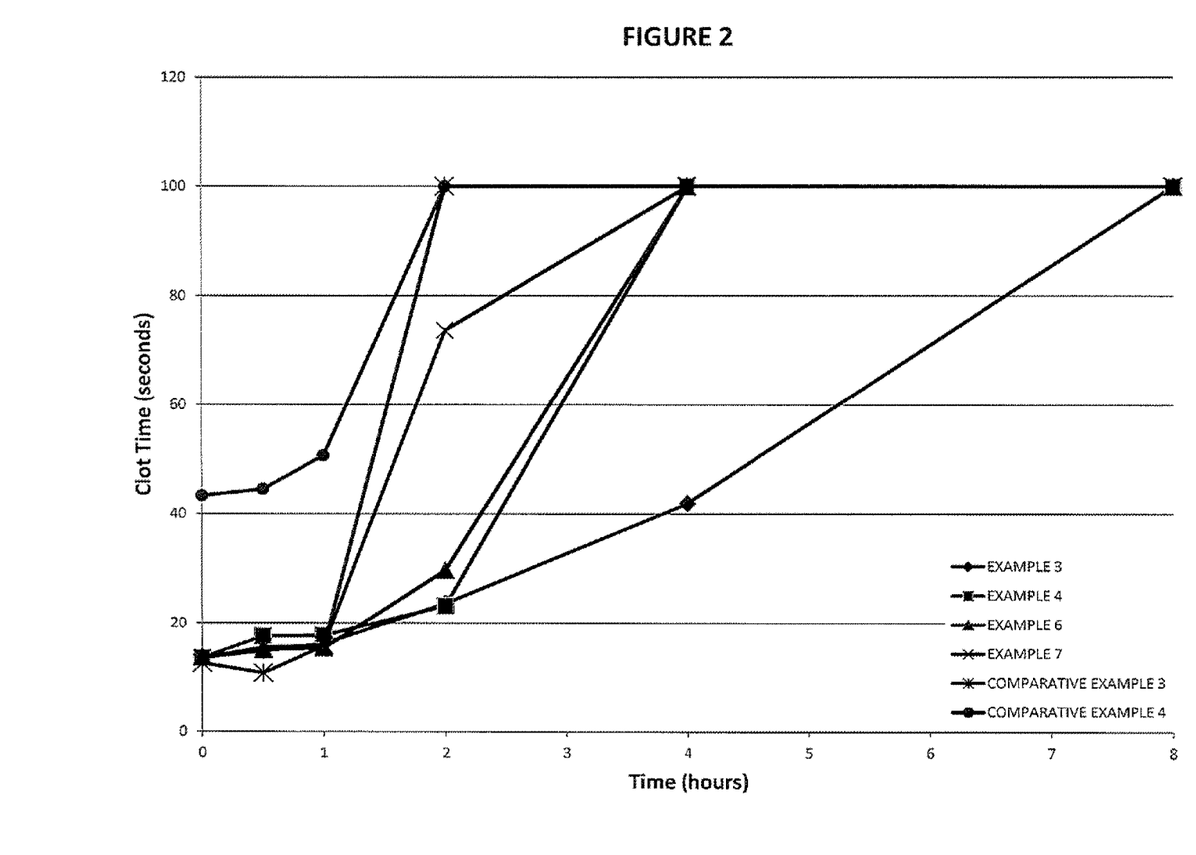
FIG. 2 depicts stability behavior at forced degradation temperature in accordance with some embodiments of the present invention.
Figure 3:
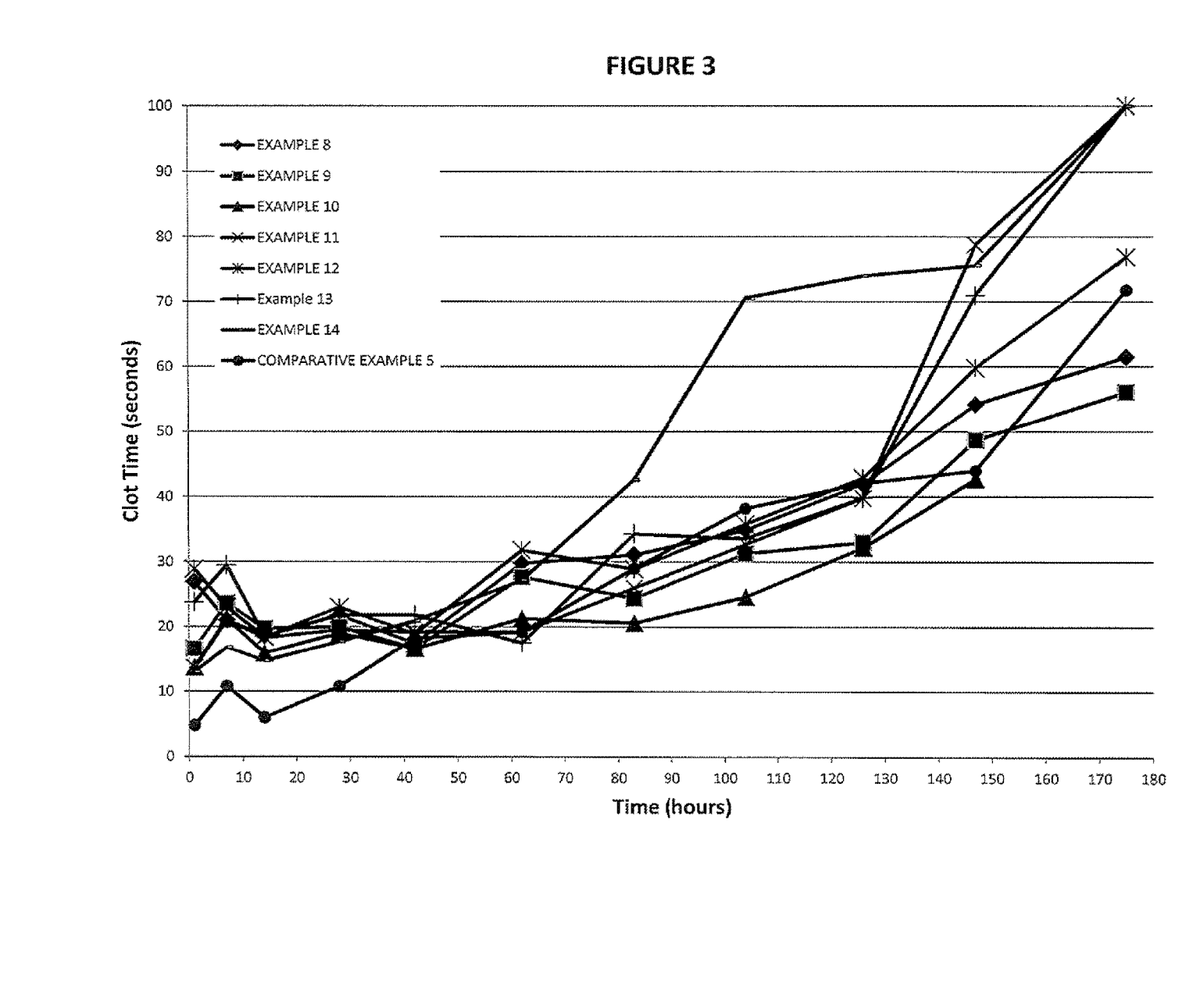
FIG. 3 depicts stability behavior at accelerated temperature in accordance with some embodiments of the present invention.

The data in Table 2 is represented graphically in FIG. 2. As illustrated in FIG. 2, Examples 4-5 at pH 5.8 are more stable than Examples 6-7 at pH 6.5. Examples 4 and 6 including sorbitol are more stable than Examples 5 and 7 including mannitol. The data as shown in Table 2 and also in FIG. 2 suggests, in some embodiments, that compositions at pH 5.8, such as in Example 4, 5 and Comparative Example 3, can be more stable than corresponding compositions at pH 6.5, such as Examples 6, 7 and Comparative Example 4. Further, the data can indicate, in some embodiments, that compositions having a sugar, such as that sorbitol in Examples 4 and 6) and mannitol in Examples 5 and 7 can be more stable than compositions that do not include a sugar, such as Comparative Examples 3 and 4. Further, the data can also indicate, in some embodiments, that compositions including sorbitol, such as Examples 4 and 6, can be more stable than compositions including mannitol, such as Examples 5 and 7.

Examples 8-9

Prepared and measured as discussed above for Example 1, except prepared at pH 5.7 and pH 6.4, respectively, and including thrombin in an amount, such that the initial thrombin activity of the composition is about 500 IU/ml.

Example 10

Prepared and measured as discussed above for Example 2, except including thrombin in an amount, such that the initial thrombin activity of the composition is about 500 IU/ml.

Example 11

Prepared and measured as discussed above for Example 3, except including thrombin in an amount, such that the initial thrombin activity of the composition is about 500 IU/ml.

Examples 12-13

Prepared and measured as discussed above for Examples 2-3, except using no first compound and a second compound of calcium acetate, and including thrombin in an amount, such that the initial thrombin activity of the composition is about 500 IU/ml.

The buffer solution of Example 12 was prepared using about 4 g of sorbitol and about 352 mg of calcium acetate in about 20 ml of water, and having a pH of about 5.74.

The buffer solution of Example 13 was prepared using about 4 g of mannitol and about 353 mg of calcium acetate monohydrate in about 20 ml of water, and having a pH of about 5.7.

Example 14

Prepared and measured as discussed above for Examples 3, except using a first compound of PEG1K and a second compound of calcium acetate monohydrate, and including thrombin in an amount, such that the initial thrombin activity of the composition is about 500 IU/ml.

The buffer solution of Example 14 was prepared using about 4 g of mannitol, about 200 mg of PEG1K and about 352 mg of calcium acetate monohydrate in about 20 ml of water, and having a pH of about 5.7.

Comparative Example 5

Commercial VITAGEL® which is measured as discussed above for Comparative Examples 1-2. Commercial VITAGEL® includes thrombin in an amount, such that the initial thrombin activity is about 800 IU/ml.

TABLE 3

Stability at 37° C.

| | | Day | | | | | |
|---|---|---|---|---|---|---|---|
| | pH | Time zero | 1 | 7 | 14 | 28 | 42 | 62 |
| | | | | Clotting time (sec) | | | | |
| Example 8 | 5.7 | 22.3 | 26.9 | 21 | 18.6 | 21.8 | 17.4 | 29.8 |
| Example 9 | 6.4 | 23.6 | 16.6 | 23.6 | 19.7 | 20 | 16.6 | 27.7 |
| Example 10 | 5.78 | 21.2 | 13.7 | 21.2 | 15.9 | 19 | 16.6 | 21.3 |
| Example 11 | 5.72 | 19.9 | 13.6 | 21 | 18.3 | 19.5 | 19.2 | 19.2 |
| Example 12 | 5.7 | 30.3 | 28.9 | 23 | 18.4 | 23 | 18.9 | 31.8 |
| Example 13 | 5.74 | 35.6 | 23.8 | 29.5 | 18.5 | 21.8 | 21.8 | 17.5 |
| Example 14 | 5.94 | 16.8 | 13 | 16.8 | 14.7 | 17.7 | 20.9 | 27.2 |
| Comparative Example 5 | 5.7 | 6.8 | 4.8 | 10.8 | 6 | 10.8 | 18.2 | 19.2 |

| | Day | | | | |
|---|---|---|---|---|---|
| | 83 | 104 | 126 | 147 | 175 |
| | Clotting time (sec) | | | | |
| Example 8 | 31.1 | 34.9 | 42 | 54.2 | 61.5 |
| Example 9 | 24.4 | 31.3 | 33 | 48.7 | 56.1 |
| Example 10 | 20.6 | 24.6 | 32.2 | 42.7 | 46.6 |
| Example 11 | 26 | 32.7 | 39.8 | 78.8 | 100 |
| Example 12 | 28.9 | 35.8 | 42.9 | 59.8 | 76.9 |
| Example 13 | 34.3 | 33.6 | 39.8 | 71 | 100 |
| Example 14 | 42.6 | 70.6 | 74 | 75.6 | 100 |
| Comparative Example 5 | 29 | 38.2 | 42.1 | 44 | 71.8 |

Figure 4:
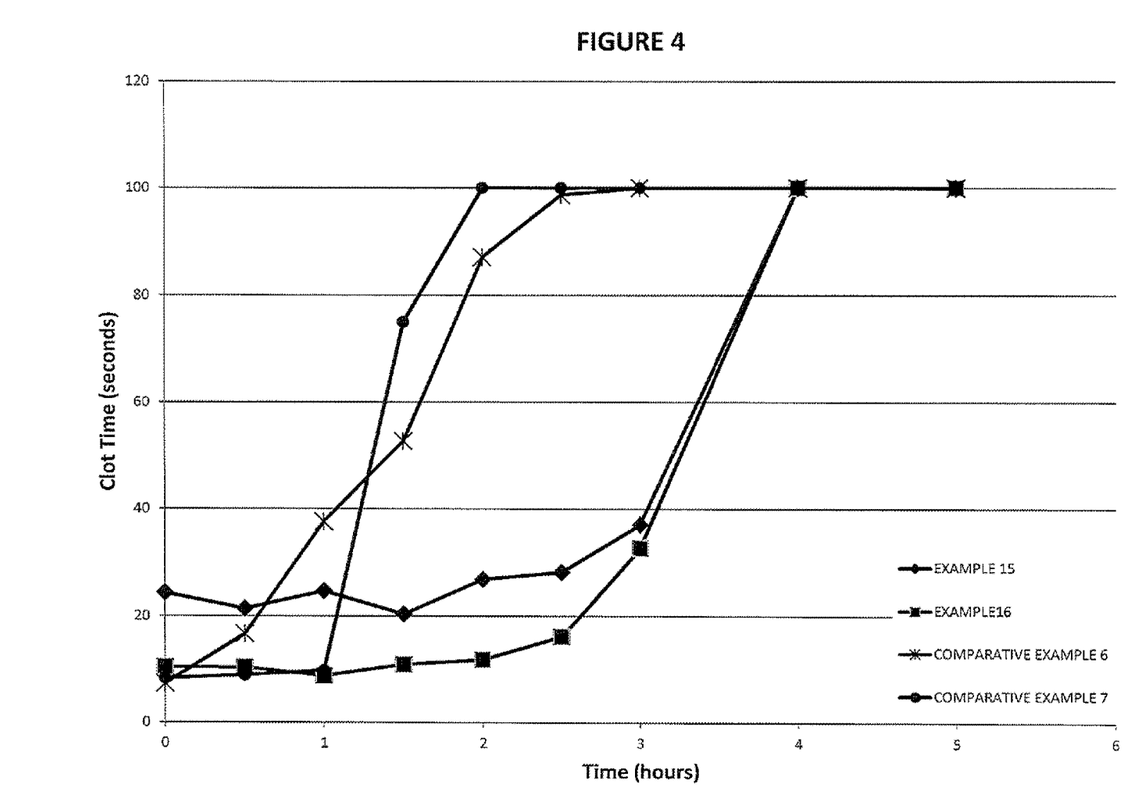
FIG. 4 depicts stability behavior at forced degradation temperature in accordance with some embodiments of the present invention.

The data from table 3 is represented graphically in FIG. 4. As shown in FIG. 4, the clotting time for Examples 10 and 14 increases from about 20 seconds to about 30 seconds between initial formation of the composition and 126 days. In contrast, the clotting time in Comparative Example 5 increases from about 8 seconds to about 40 seconds between initial formation and 126 days. The compositions of the present invention, such as Examples 8-14, can have improved thrombin stability for the storage period over commercial VITAGEL® (Comparative Example 5), even though the compositions have a lower initial thrombin activity compared to commercial VITAGEL®. The compositions of the present invention, such as in Examples 8-14, although having an initial thrombin activity (about 500 IU/ml) below that of commercial VITAGEL®, can exhibit a reduced rate of degradation in thrombin activity. In some embodiments, the compositions, such as Examples 8-10 can surpass the thrombin activity of commercial VITAGEL® during the storage period.

Example 15

Prepared and measured as discussed above for Example 2, except including thrombin in an amount, such that the initial thrombin activity of the composition is about 500 IU/ml, and incubation and measurement temperature of about 60° C.

Example 16

Prepared and measured as discussed above for Example 2, except including recombinant thrombin in an amount, such that the initial thrombin activity of the composition is of about 500 IU/ml, and incubation and measurement temperature of about 60° C.

Comparative Example 6

Prepared and measured as discussed above for Comparative Example 1, except including thrombin in an amount, such that the initial thrombin activity of the composition is of about 800 IU/ml, and incubation and measurement temperature of about 60° C.

Comparative Example 7

Preparation of a Buffer Solution

A buffer solution having about 200 mg of PEG(3350), about 78 mg of L-histidine, about 876 mg of the NaCl, about 444 mg of the CaCl$_2$, about 3 g of sucrose, and about 4 g of mannitol in about 100 ml of water was prepared. Using about 0.01N HCl solution, the pH of the buffer solution was adjusted to about 5.7.

The composition was prepared and measured as discussed above for Comparative Example 1, except including recombinant thrombin in an amount, such that the initial thrombin activity of the composition is about 800 IU/ml, and incubation and measurement temperature of about 60° C.

TABLE 4

Stability at 60° C.

| | pH | 0 | 0.5 | 1 | 1.5 | 2 | 2.5 | 3 | 4 | 5 |
|---|---|---|---|---|---|---|---|---|---|---|
| | | | | | Clotting time (sec) | | | | | |
| Example 15 | 5.7 | 24.35 | 21.4 | 24.7 | 20.4 | 26.9 | 28.2 | 37.1 | 100 | 100 |
| Example 16 | 5.7 | 10.4 | 10.3 | 8.8 | 10.9 | 11.8 | 16.1 | 32.7 | 100 | 100 |
| Comparative example 6 | 5.6 | 7.3 | 16.6 | 37.6 | 52.7 | 87.1 | 98.7 | 100 | 100 | 100 |
| Comparative example 7 | 5.7 | 8.3 | 8.9 | 9.8 | 75.05 | 100 | 100 | 100 | 100 | 100 |

The data from Table 4 is represented graphically in FIG. 4. As shown in FIG. 4, Examples 6 and 7 using bovine and recombinant thrombin, respectively, maintain a clotting time below about 40 seconds for up to about 3 hours at incubation of about 60° C. In contrast, Comparative Examples 6 and 7 fail to maintain a clotting time below about 40 seconds after 1.5 hours. The data shown in Table 4 and FIG. 4 can indicate, in some embodiments, that a composition including sorbitol, sodium acetate, and calcium propionate can stabilize both recombinant thrombin (Example 16) and also bovine thrombin (example 15) with about the same degree of stability. Further, the compositions including sorbitol, such as Examples 15 and 16 can provide superior stability to a composition including histidine, such as Comparative Example 7. The current vitagel buffer Comparative Example 6), using the same buffer solution as used in commercial VITAGEL®, and Comparative Example 7 provide minimum stability to bovine and recombinant thrombin, respectively, but are clearly inferior to the compositions used in Examples 15 and 16 as shown in Table 4 and FIG. 4.

The compositions of the present invention stabilize thrombin of both bovine and human recombinant origin in a liquid state. The compositions can be effective at stabilizing pepsinized microfibrillar thrombin. The compositions can stabilize thrombin in at least a pH range of about 5.5 to about 6.5. The compositions of the present invention can reduce costs due to improved stability of thrombin.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An aqueous buffer solution, comprising:
   sorbitol;
   a first compound; and
   a second compound,
   wherein the first compound is represented by the following Formula I:

Formula I wherein $R_1$ is —$CH_3$ and wherein $M^+$ is a sodium ion ($Na^+$);
   wherein the second compound is represented by the following Formula II:

Formula II wherein $R_2$ is $CH_2CH_3$ and wherein $M^{2+}$ is a calcium ion ($Ca^{2+}$), and
   wherein the buffer solution does not include a chloride-containing salt.

2. The buffer solution of claim 1, wherein the pH of the composition ranges from about 5.0 to about 8.5.

3. An aqueous buffer solution, comprising:
   sodium succinate,
   calcium propionate, and
   sorbitol
   wherein the buffer solution does not include a chloride-containing salt.

4. The buffer solution of claim 3, wherein the sodium succinate is dibasic.

5. The buffer solution of claim 1, wherein an amount of the first compound ranges from about 1 mg/ml to about 50 mg/ml.

6. The buffer solution of claim 1, wherein an amount of the second compound ranges from about 1 mg/ml to about 50 mg/ml.

7. The buffer solution of claim 1, wherein an amount of the sorbitol ranges from about 2.5 wt % to about 20 wt % of the buffer solution.

8. A composition including pepsinized microfibrillar collagen and thrombin in the aqueous buffer solution of claim 1, wherein an initial thrombin activity ranges from about 400 to about 500 units of enzyme activity per milliliter of buffer solution.

9. The composition of claim 8, where the thrombin is bovine thrombin or recombinant thrombin.

10. The composition of claim 8, wherein an amount of the sorbitol ranges from about 0.1 to about 10 wt % of the composition.

11. The composition of claim 8, wherein an amount of the first compound ranges from about 0.1 wt % to about 5 wt % of the composition, and wherein an amount of the second compound ranges from about 0.1 wt % to about 5 wt % of the composition.

12. The buffer solution of claim 3, wherein an amount of the sodium succinate ranges from about 1 mg/ml to about 50 mg/ml.

13. The buffer solution of claim 3, wherein an amount of the calcium propionate ranges from about 1 mg/ml to about 50 mg/ml.

14. The buffer solution of claim 3, wherein an amount of the sorbitol ranges from about 2.5 wt % to about 20 wt % of the buffer solution.

15. A composition including pepsinized microfibrillar collagen and thrombin in the aqueous buffer solution of claim 3, wherein an initial thrombin activity ranges from about 400 to about 500 units of enzyme activity per milliliter of buffer solution.

16. The composition of claim 15, where the thrombin is bovine thrombin or recombinant thrombin.

17. The composition of claim 15, wherein an amount of the sorbitol ranges from about 0.1 to about 10 wt % of the composition.

18. The composition of claim 15, wherein an amount of the sodium succinate ranges from about 0.1 wt % to about 5 wt % of the composition, and wherein an amount of the calcium propionate ranges from about 0.1 wt % to about 5 wt % of the composition.

* * * * *